(12) United States Patent
Morgan et al.

(10) Patent No.: US 7,392,842 B2
(45) Date of Patent: Jul. 1, 2008

(54) PROPPANT SUSPENSION TESTING DEVICES AND METHODS OF USE

(75) Inventors: Rickey L. Morgan, Duncan, OK (US); Johnny W. Johnson, Duncan, OK (US); Ronnie G. Morgan, Waurika, OK (US); Harold G. Walters, Duncan, OK (US)

(73) Assignee: Halliburton Energy Services, Inc., Duncan, OK (US)

( * ) Notice: Subject to any disclaimer, the term of this patent is extended or adjusted under 35 U.S.C. 154(b) by 200 days.

(21) Appl. No.: 11/246,816

(22) Filed: Oct. 7, 2005

(65) Prior Publication Data

US 2007/0079961 A1  Apr. 12, 2007

(51) Int. Cl.
*E21B 43/267* (2006.01)
*G01N 11/14* (2006.01)

(52) U.S. Cl. .................. 166/250.1; 73/54.28; 73/54.39

(58) Field of Classification Search .............. 166/250.1; 73/54.28, 54.01, 54.23, 54.33, 54.39, 152.19, 73/152.22, 54.32
See application file for complete search history.

(56) References Cited

U.S. PATENT DOCUMENTS

| | | | | |
|---|---|---|---|---|
| 2,626,786 | A | * | 1/1953 | McGlothlin .............. 366/181.6 |
| 3,269,171 | A | * | 8/1966 | Bruss et al. ................. 73/54.39 |
| 4,283,938 | A | * | 8/1981 | Epper et al. ................ 73/54.31 |
| 4,653,313 | A | * | 3/1987 | Sabins et al. ............... 73/54.39 |
| 5,799,734 | A | | 9/1998 | Norman et al. ............. 166/278 |
| 6,782,735 | B2 | | 8/2004 | Walters et al. ............. 73/52.28 |
| 6,782,753 | B1 | | 8/2004 | Immer et al. ................... 73/744 |
| 6,997,045 | B2 | * | 2/2006 | Wallevik et al. ........... 73/54.28 |
| 2004/0149019 | A1 | * | 8/2004 | Johnson et al. ............ 73/54.28 |

OTHER PUBLICATIONS

A. Thesing, Entitled New Device for Rheology Measurements of Proppant-Laden Fluids With the Fann 50 Viscometer, SPE 58759, 2000.

(Continued)

*Primary Examiner*—William P Neuder
(74) *Attorney, Agent, or Firm*—Robert A. Kent; Crutsinger & Booth, LLC (57) ABSTRACT

An apparatus for testing a rheological property of a fluid with a particulate includes: (a) a receptacle having a cylindrical side wall enclosed by a bottom wall defining a cavity for receiving a fluid to be tested; (b) an axial support adapted to be positioned in the cavity of the receptacle, whereby relative rotational motion can be imparted to the receptacle and the axial support; (c) at least one inward projection extending inward from an inside surface of the receptacle; (d) at least one outward projection extending outward from the axial support; and (e) at least one projection for directing fluid flow that has at least one major surface angled or curved upward. A method of testing a rheological property of a fluid with a particulate includes: (a) placing a sample of the fluid and the particulate in the apparatus; (b) imparting relative rotational motion to the receptacle and the axial support; and (c) measuring the torque between the receptacle and the axial support. A method of fracturing a subterranean formation penetrated by a well includes: (a) placing a sample of a fracturing fluid and a particulate in the apparatus; (b) imparting relative rotational motion to the receptacle and the axial support; (c) measuring the torque between the receptacle and the axial support; (d) adjusting the conditions for mixing the fracturing fluid and the particulate in response to the measured torque; and (e) injecting the fluid and particulate into the well at a sufficient rate and pressure to fracture the formation.

5 Claims, 4 Drawing Sheets

OTHER PUBLICATIONS

D. L. Lord, Entitled Helical Screw Rheometer: a New Tool for Stimulation Fluid Evaluation, SPE 18213, 1998.

D. L. Lord, et al., Entitled Real-Time Fracturing Fluid Rheology Mesurements With the Helical Screw Rheometer, SPE 19734, 1989.

* cited by examiner

PROPPANT SUSPENSION TESTING DEVICES AND METHODS OF USE

CROSS-REFERENCE TO RELATED APPLICATIONS

Not applicable

STATEMENT REGARDING FEDERALLY SPONSORED RESEARCH OR DEVELOPMENT

Not Applicable.

REFERENCE TO A MICROFICHE APPENDIX

Not applicable.

BACKGROUND

This invention relates generally to improvements in devices and methods that are used to test the rheology of fluids, especially ones containing or mixed with particulate material (subsequently referred to simply as "particulate"). The particular field of use is the oil and gas industry.

Various types of fluids are used in the oil and gas industry. Non-limiting examples include drilling muds, cement, gravel slurries, and stimulation treating fluids. Such fluids are typically pumped into oil or gas wells in known manners. It is desirable to know various characteristics of the fluids to determine how such fluids will act upon being pumped and placed in, or circulated through, the wells.

Rheology is the branch of physics dealing with the deformation and flow of matter. Viscosity, elasticity, and consistency are rheological characteristics that sometimes need to be measured for a given fluid. Such rheological characteristics can be non-linear functions of time, temperature, and pressure. Known devices used to test fluids for these characteristics include viscometers, rheometers, and consistometers.

Some fluids used in oil or gas wells carry particulate, and it is typically desired that such fluids support the particulate in suspension for at least some period of time. That is, the particulate is preferably dispersed throughout the volume of a particular fluid during at least part of the time the fluid is used in a well. For example, a fracturing fluid might include a base fluid that can be crosslinked to a gel form so that it can better support a quantity of particulate referred to as a propping agent or proppant. An example of a propping agent or proppant is sand. The fracturing fluid is a fluid that preferably initially increases in viscosity as the fluid approaches the well's treatment zone, to suspend or support the proppant in the fluid during the time the mixture is pumped into a well. The fracturing fluid later "breaks" or decreases in viscosity so that it can easily flow back out of the well, while leaving a clean proppant pack in the fracture. The pumping is under pressure sufficient for the fluid to hydraulically fracture a selected zone of the earth traversed by the well. After fracturing, the fluid may be flushed out with the flow of hydrocarbons from the fractured zone, but the propping agent preferably remains in place to prop the fractures open.

Proppant transport is a function of: (1) wellbore and fracture geometry; (2) volumetric rate; (3) proppant size, concentration, and specific density; and (4) carrier-fluid rheology.

A typical fluid used to transport particulate has a viscosity that changes during the time the fluid is used in a well. Viscosity is defined as the ratio of shear stress to shear rate (velocity gradient). If this ratio changes with shear rate, this may be referred to as "apparent viscosity function." Viscosity is one parameter of the fluid that defines the fluid's ability to support the particulate in suspension. However, to measure a single viscosity point or the apparent viscosity function does not directly indicate the time during which the fluid will support particulate in suspension and the time during which the fluid will not. That is, a measurement that merely shows a changing viscosity does not indicate when the particulate is in suspension within the fluid and when it is not (i.e., when the particulate has settled out of the fluid).

Elasticity is another parameter of the fluid that defines the fluid's ability to support the particulate in suspension.

Instruments such as Fann Model 50 viscometers are available for measuring viscosity, including at high temperatures and pressures, but elasticity is much more elusive to measure. Additionally, most viscometers, such as the Fann Model 50, are designed only to handle the "clean fluid systems," e.g., without proppant. It has generally been assumed that higher viscosities will do a better job of transporting proppant, as well as generating the desired fracture geometry.

Several rheological properties directly impact a fracturing fluid's performance: (1) apparent viscosity function, (2) yield stress, (3) dynamic viscosity, (4) rheomalaxis (irreversible thixotrophy), (5) viscoelasticity (for example G', G", tangent delta), and (6) the related issue of turbulent-drag reduction. In laboratory research, sample volume is often very limited, thus necessitating rheological testing and evaluation of small quantities. Also, most bench-top rheometers use batch mode, that is, small samples are placed in a testing chamber as opposed to flow-through testing, as is the case for pipe viscometers. This presents the challenge of simultaneously: (a) Imparting viscometric shear history that simulates the wellbore travel path; (b) Not exceeding the proper mechanical energy input—the bench-top batch process should impart about the same amount of integrated work as the wellbore path; and (c) Maintaining satisfactory thermal balance, e.g., being sure not to create localized "hot spots" in the bench-top process because of its batch mode of operation.

In the case of most polymer-based fracturing fluids, the capability to transport proppant is directly related to their "rheological equations of state (RES)." Extent of crosslinking, breaking, shear history, and volume-average shear rate are major factors affecting a fluid's RES.

Where viscous drag dominates, as in the classical case of a tow-winged vertical fracture with parallel-plate geometry, the challenge in proppant transport is to ensure that vertical settling time is much greater than horizontal travel time. Sufficient vertical settling time allows the particle to reach a maximum horizontal distance, thus avoiding a duning effect. Preferably, the horizontal transport time is at least 50 times greater than the vertical settling time.

In the case of crosslinked gels, the elastic forces are designed to dominate, preventing any substantial viscous settling during the fracturing and placement of proppant. It is believed that a minimum value of G' (oscillatory elastic storage modulus) of 10 to 12 Pa's is sufficient for most 20/40 frac sands.

The complex viscoelastic nature of crosslink fracturing fluids presents a dilemma for the fracturing rheologist. Conventional rheometers are designed for measuring viscoelastic properties through well-controlled oscillatory deformations that are small, non-destructive, and within the linear elastic range. However, the actual fracturing process involves large amounts of shear strain of multiple orders of magnitude, well beyond the linear elastic range. As the breaker reaction begins to dominate, the transport mechanism shifts from elastic to viscous, leading to settling caused by the low viscosity of the broken fluid system.

The Fann Model 50 viscometer was designed for characterizing fracturing gels under simulated downhole temperature-time conditions. However, the Model 50 and most other bench-top viscometers/rheometers are not adequately equipped to handle proppant-laden fluids. In the case of concentric cylinders, the centrifugal forces tend to stratify the particles, thus resulting in nonrelevant data. In cone-plate and plate-plate viscometers, the small gaps necessary to provide torque sensitivities result in "particle jamming." Additionally, the large density differences between most proppants and conventional fracturing fluids can result in settling during testing, thus producing unreliable results.

U.S. Pat. No. 6,782,735 issued Aug. 31, 2004 and entitled Testing Device and Method for Viscosified Fluid Containing Particulate Material, which is incorporated herein by reference for all purposes, discloses a device and a method for testing a viscosified fluid containing particulate that indicate when the particulate is in suspension within the fluid and when it is not. The device and method stir the fluid and particulate mixture for a time during which the viscosity of the fluid changes such that during a first period of the stirring time substantially all the particulate remains suspended in the fluid and during a second period of the stirring time substantially all the particulate settles out of suspension in the fluid. A signal is generated during the first and second periods such that the signal has a characteristic that changes from the first period to the second period to indicate the change in particle carrying ability of the fluid. Other characteristics, including crosslinking time, can also be determined. A test chamber includes interacting projections extending from the inner surface of a cup receiving the fluid and from an axial support extending into the fluid in the cup. U.S. Pat. No. 6,782,735, Abstract. For example, a viscometer according to U.S. Pat. No. 6,782,735 can be uniquely designed to keep highly concentrated dense particles suspended in fluids while measuring "volume-averaged shear stresses and shear rates." However, the devices and methods disclosed in U.S. Pat. No. 6,782,735 must be loaded with pre-crosslinked fracturing fluid along with the particulate and breakers such that the proppant is suspended during mounting and testing.

In addition, well fracture fluids are sometimes blended at the well site with the proppant while the fluids are in the "un-crosslinked" state and are at the same time mixed or contacted with chemicals called "crosslinkers" that cause crosslinking after a specified temperature-time history. Un-crosslinked well fluids are not designed to support proppant and attempts to test with conventional equipment results in errors due to proppant settling or fallout. For example, conventional viscometers and rheometers, are not capable of accepting fluids with particulates the size of proppants, ranging from a few hundred microns to 1,000 microns. Usually the clearances between the surfaces used to establish a known shear rate, are on the same order of magnitude as proppants. In the cases in which "large gap devices" have been employed to solve this problem, centrifugal forces and local vortices cause significant error due to sample stratification of the proppant. On the other hand, conventional testing devices that provide constant agitation do not prevent the particle settling, and may operate in the turbulent regime.

Accordingly, there is a need for a device and method to measure the viscous and elastic properties of mixtures of un-crosslinked well fluids, both with and without particulate, including before, during and after crosslinking and before, during, and after breaking, under dynamic conditions at elevated temperatures and pressures at a variety of shear rates and in such a way as to directly indicate particle transport, suspension, and settling.

At least one embodiment of such a testing device and method preferably should also be suitable for use at a well site to properly measure the rheological properties of fluid mixtures before, during, and after crosslinking and breaking.

SUMMARY OF THE INVENTION

According to one aspect of the invention, an apparatus is provided for testing a rheological property of a fluid with a particulate. According to this aspect of the invention, the apparatus comprises: (a) a receptacle having a cylindrical side wall enclosed by a bottom wall defining a cavity for receiving a fluid to be tested; (b) an axial support adapted to be positioned in the cavity of the receptacle, whereby relative rotational motion can be imparted to the receptacle and the axial support; (c) means for stirring fluid and particulate in the cavity when relative rotational motion is imparted to the receptacle and the axial support; and (d) means for directing rotational flow of fluid and particulate in the cavity toward an axial direction when the fluid and particulate is being stirred.

According to another aspect of the invention, an apparatus is provided for testing a rheological property of a fluid with a particulate. According to this aspect of the invention, the apparatus comprises: (a) a receptacle having a cylindrical side wall enclosed by a bottom wall defining a cavity for receiving a fluid to be tested; (b) an axial support adapted to be positioned in the cavity of the receptacle, whereby relative rotational motion can be imparted to the receptacle and the axial support; (c) at least one inward projection extending inward from an inside surface of the receptacle; (d) at least one outward projection extending outward from the axial support; and (e) at least one projection for directing fluid flow that has at least one major surface angled or curved upward.

A method of testing a rheological property of a fluid with a particulate is also provided. The method comprises the steps of: (a) placing a sample of the fluid and the particulate in an apparatus; (b) imparting relative rotational motion to the receptacle and the axial support; and (c) measuring the torque between the receptacle and the axial support. According to one aspect of the method invention, the apparatus comprises: (i) a receptacle having a cylindrical side wall enclosed by a bottom wall defining a cavity for receiving a fluid to be tested; (ii) an axial support adapted to be positioned in the cavity of the receptacle, whereby relative rotational motion can be imparted to the receptacle and the axial support; (iii) means for stirring fluid and particulate in the cavity when relative rotational motion is imparted to the receptacle and the axial support; and (iv) means for directing rotational flow of fluid and particulate in the cavity toward an axial direction when the fluid and particulate is being stirred.

According to another aspect of the method invention, the apparatus comprises: (i) a receptacle having a cylindrical side wall enclosed by a bottom wall defining a cavity for receiving a fluid to be tested; (ii) an axial support adapted to be positioned in the cavity of the receptacle, whereby relative rotational motion can be imparted to the receptacle and the axial support; (iii) at least one inward projection extending inward from an inside surface of the receptacle; (iv) at least one outward projection extending outward from the axial support; and (v) at least one projection for directing fluid flow that has at least one major surface angled or curved upward.

According to yet another aspect of the invention, a method of fracturing a subterranean formation penetrated by a well is provided. According to this aspect, the method comprises the steps of: (a) placing a sample of a fracturing fluid and a particulate in an apparatus according to the invention; (b) imparting relative rotational motion to the receptacle and the axial support; (c) measuring the torque between the receptacle and the axial support; (d) adjusting the conditions for mixing the fracturing fluid and the particulate in response to the measured torque; and (e) injecting the mixed fluid and particulate into the well at a sufficient rate and pressure to fracture the subterranean formation.

Therefore, from the foregoing, it is a general object of the present invention to provide improved devices and methods for testing viscous and/or elastic fluids, including ones containing particulate. Other and further objects, features and advantages of the present invention will be readily apparent to those skilled in the art when the following description of the preferred embodiments is read in conjunction with the accompanying drawings.

DETAILED DESCRIPTION

The present invention meets the foregoing needs by providing novel and improved devices and method for accurately testing viscous and/or elastic fluids, including ones containing particulate before, during, and after cross-linking and before, during, and after breaking. Such devices and methods directly indicate time periods and simulated conditions during which a tested fluid is supporting particulate in suspension and when the tested fluid is not (i.e., when the particulate is settling out of suspension). In addition, the present invention meets the forgoing needs by providing the means with which to continuously monitor the "suspension state" of the fluid system, thus providing for understanding the dynamics that drive particle settling.

In general, an apparatus according to the invention is or includes a test cell for use in a viscometer having fins or blades, as hereinafter described in more detail, that function to provide vertical lift and homogenization of the laden particulate while in non-crosslinked fluids when sufficient rotational velocity is applied. The number, angle, curvature, and spacing of these fins or blades can be designed so as to provide suspension under volume average shear rates similar to fracture transport in well fracturing procedures. A presently preferred shear range is about 10 to about 100 1/sec.

The apparatuses according to the invention offer several advantages over prior devices and methods. One advantage is the ability to load the test cell with un-crosslinked or pre-crosslinked fracturing fluids along with proppant. Of course, the fracturing fluids can also include buffers, crosslinkers, breakers, and other well treatment fluid additives, thus simulating surface blending processes. Another advantage is the ability to simulate the blending of the ingredients under shear, temperature, and pressure that simulate travel of the mixture through the well bore during a fracturing treatment. Another advantage is the ability to study the effects of particle-to-particle settling and particle-to-fluid shear history effects. Yet another advantage is the ability to simulate gravel packing operations. These advantages are provided while maintaining the accurate rheological measurements achievable with the devices and methods as previously disclosed in U.S. Pat. No. 6,782,735. This can be useful, for example, to simulate additional job processes of a fracturing treatment for a subterranean formation, such as mixing processes on the surface at the well head, injection processes through the well bore, and injection processes into the formation. Thus, this provides the ability to study the effects of cross-linking kinetics under temperature-pressure-shear in addition to the breaking kinetics. Furthermore, the devices and methods according to the invention can be useful to measure highly elastic clean fluids, which are currently difficult to measure in standard coquette geometry due to rod climbing effects. It is to be understood, of course, that not every design according to the present invention is expected to be capable of providing all of these advantages.

A particular implementation of the device of the present invention may be referred to as a high-pressure, high-temperature mixer viscometer that can measure viscous and elastic properties and crosslink and particulate transport time. This implementation includes a paddle type of mixing device which has one or more flags, paddles, or vanes which rotate in or around the fluid to be tested and one or more flags, paddles, or vanes in a torque sensing structure. According to a particular feature of the present invention, at least one of the flags, paddles, or vanes is arranged to cause fluid and solids in the mixer to circulate axially to minimize particulate settling or fall out. The device is capable of measuring varying volume average shear rates and volume average shear stresses, signifying varying volume average viscosities and/or elasticities, and is especially useful at low shear rates. Preferably, this device can condition the fluid under test at low, ambient, and elevated temperatures and pressures. This device provides an output that can be used to measure or indicate viscous and elastic properties of the test fluid (which can be with or without particulate material), the change in fluid properties with time (e.g., crosslink time), particle transport (particle suspension and particle settling), and particle-to-particle interactions and degree of adhesive coating on particles (e.g., higher torque readings for more particle-to-particle interaction, such as from higher particle concentrations, or for increased adhesive coating).

The present invention provides a mixer viscometer which comprises: a closed receptacle having a cavity to receive a volume of fluid or fluid mixture containing particulate; means for closing the cavity fluid is placed therein such that the closed cavity defines a continuous test chamber which can be pressurized above atmospheric pressure; means for stirring the fluid in the test chamber such that particulate in the fluid is prevented from settling and remains suspended in the fluid during; and means for generating a signal in response to the stirring. The means for stirring preferably includes at least one projection extending into the cavity from an inner surface of the receptacle defining the cavity and wherein the projection has an axially inclined surface to provide an axial component to the stirring action.

Another definition of the present invention is as a particle transport capability detector apparatus which comprises: a viscometer including a viscometer cup and further including an axial shaft disposed within the cup when a fluid to be tested is in the cup; at least one projection extending laterally outward from the axial shaft of the viscometer; and at least one projection extending laterally inward from an inner surface of the viscometer cup, wherein the projections effect stirring of the fluid in the cup in response to rotation of at least one of the cup or axial shaft of the viscometer. In addition, the detector has at least one projection extending from the side wall of the cup or extending from the axial shaft that has an axially inclined surface to provide an axial flow component to the stirring action of fluid in the cup in response to rotation of at least one either the cup or axial shaft of the viscometer.

Another definition of the present invention is as a particle transport capability detector apparatus which comprises: a viscometer including a viscometer cup and further including an axial shaft disposed within the cup when a fluid to be tested is in the cup; at least one projection extending laterally outward from the axial shaft of the viscometer; and at least one projection extending laterally inward from an inner surface of the viscometer cup, wherein the projections effect stirring of the fluid in the cup in response to rotation of at least one of the cup or axial shaft of the viscometer. In addition, the detector has at least one projection extending from the bottom of the cup having an axially inclined fluid contacting surface thereon to provide an axial flow component to the stirring action of the fluid in the cup in response to relative rotation between the cup and shaft.

According to a particular feature or the present invention, an improved measuring device is designed to mix and suspend or resuspend a fluid mixture containing particulate materials such as proppant depending on the speed of rotation. A "resuspend" is defined as the phenomena that occurs when proppant or particles have settled to the bottom of the cup, and which can be restored to pre-settling state of suspension by means of imparting unique movement of the fluid and particles by way of angled vanes and/or impellers. Faster speeds will suspend and slower speeds will allow it to settle. The settling and compaction of the proppant in the bottom of the cup gives the increase in torque.

The ability to resuspend is especially useful in starting a test with a delayed crosslinker where the fluid does not initially suspend the proppant. This feature also is important in that it facilitates the use of speed and temperature profiles so as to closely simulate movement of fluid and particles during a normal fracture job, including, but not limited to: surface blending and suspension, which is primarily achieved by maintaining critical flow velocities; well bore travel path (shear and thermal histories); flow through perforations (shear and thermal histories); and finally flow down the fracture to the particles final resting place. It also provides the ability to simulate all of this movement under dynamic conditions of crosslinking and breaking phenomena. Another new advantage to the present invention is that it provides the ability to take multiple settling measurements when the fluid is weakly or not completely crosslinked. Also, late in a test of cross-linked fluid with breaker, the proppant can be resuspended to measure the settling rate. Further, multiple measurements with a linear base gel (not crosslinked) could be made for repeatability and accuracy. The resuspension capability makes this device particularly adapted for field use. For example, the apparatus can be used in fracturing procedures for oil or gas wells.

The present invention also provides methods of testing for particulate transport time of a fluid containing particulate. The method comprises stirring, for a time during which the viscosity or elasticity of the fluid changes, a fluid containing particulate such that during testing the particulate remains suspended in the fluid. The method further comprises generating a signal during the first and second periods such that the signal has a characteristic that changes from the first period to the second period to indicate the change in particulate carrying ability of the fluid.

As used herein and in the appended claims, the words "comprise," "has," and "include" and all grammatical variations thereof are each intended to have an open, non-limiting meaning that does not exclude additional elements or parts of an assembly, subassembly, or structural element.

If there is any conflict in the usages of a word or term in this specification and one or more patent or other documents that may be incorporated herein by reference, the definitions that are consistent with this specification should be adopted.

A type of fluid with which the present invention can be used is referred to as a viscous and/or elastic fluid whose viscosity and elasticity change over time, or may remain constant at a given shear rate, temperature, and pressure. One such fluid is a viscoelastic fluid that may typically go through different phases over time; for example, from an initial uncrosslinked state, to a crosslinked elastic state, to a "broken gel state" giving rise to a viscous settling state. The particulate to be used in the fluid can be, for example, sized sand, resin coated sand, sintered bauxite beads, metal beads or balls, ceramic particles, glass beads, polymer resin beads, ground nut shells and the like. The particulate size may be of any suitable size, with typical sizes being within the range from about 8 to about 170 on the U.S. Sieve Series scale. The foregoing are non-limiting examples. A more general statement about a mixture for which the present invention is particularly intended is that it is a mixture of a particulate and a fluid which during one period of time is able to support the quantity of particulate in suspension under a stirring action but which during another period of time is unable to support the particulate in suspension even under the stirring action. The invention also measures viscous and/or elastic properties of the fluid itself without sand. Examples include drilling muds, cement slurries, and stimulation treating fluids used in the oil and gas industry.

Figure 1:
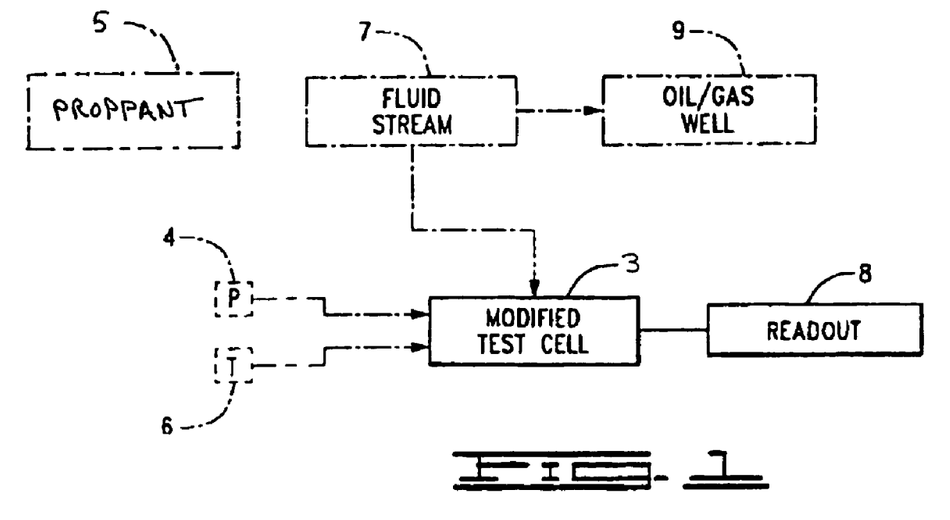
FIG. 1 is a block diagram of a viscometer having a modified test cell implementing a preferred embodiment of the present invention, which viscometer is illustrated in an environment at an oil or gas well site and which viscometer can be an open-cup type or a high-pressure and/or high-temperature type.

One preferred embodiment device of the present invention that tests a fluid such as described above is implemented with a high-pressure (above atmospheric), high-temperature (above 212 degree F.) viscometer which includes a receptacle to receive the fluid to be tested and which also includes a support that is disposed in the receptacle (and thus also in the fluid) when the fluid is in the receptacle to be tested. Such a viscometer can be a conventional one (e.g., a Fann model 50 viscometer) but adapted to the present invention by a modified test cell 3. The present invention can also be used with, or incorporate, a conventional open-cup or atmospheric viscometer (e.g., a Fann model 35 viscometer), but also adapted by a modified test cell 3. In either case, this modified test cell 3 includes at least one projection extending laterally inward from an inner surface of the receptacle mentioned above and forming part of the modified test cell 3. The modified test cell 3 also includes at least one projection extending laterally outward from the support mentioned above. Such device of the present invention is depicted in FIG. 1 and can otherwise comprise conventional components of a high-pressure, high-temperature viscometer, including pressure control 4, temperature control 6, and readout 8, or of an atmospheric type viscometer that does not have at least the pressure control 4. As also shown in FIG. 1, either embodiment can be used at a well site to receive in real time a sample of the mixture from a fluid stream 7 flowing into an oil or gas well 9. In addition, the test cell 3 can also receive a sample of the proppant 5 for mixing with a sample of the fluid stream 7 and testing the rheological properties of the mixture.

Figure 2:
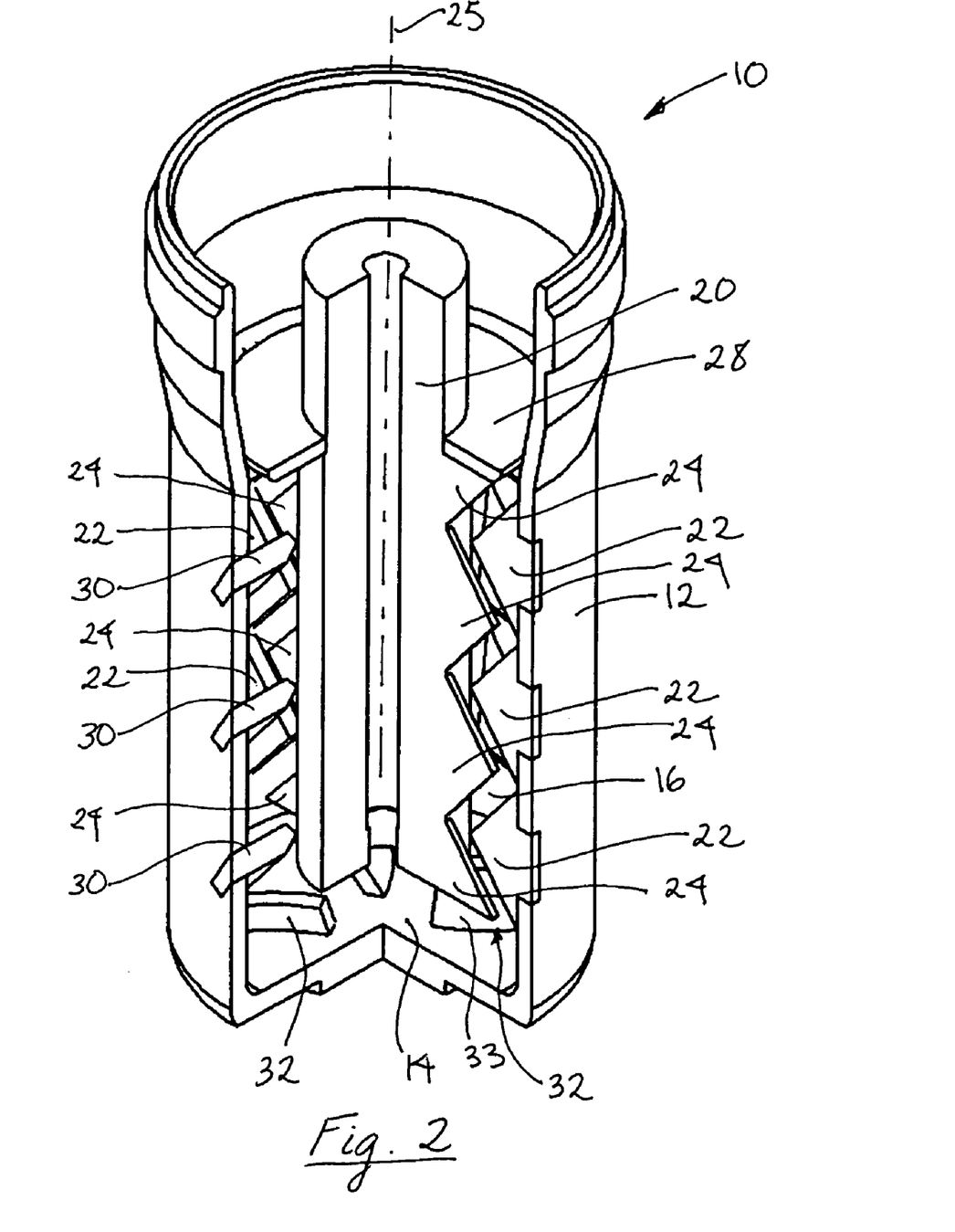
FIG. 2 is a schematic, perspective cut-away illustration of the modified test cell of a particular implementation of the preferred embodiment.
Figure 3:
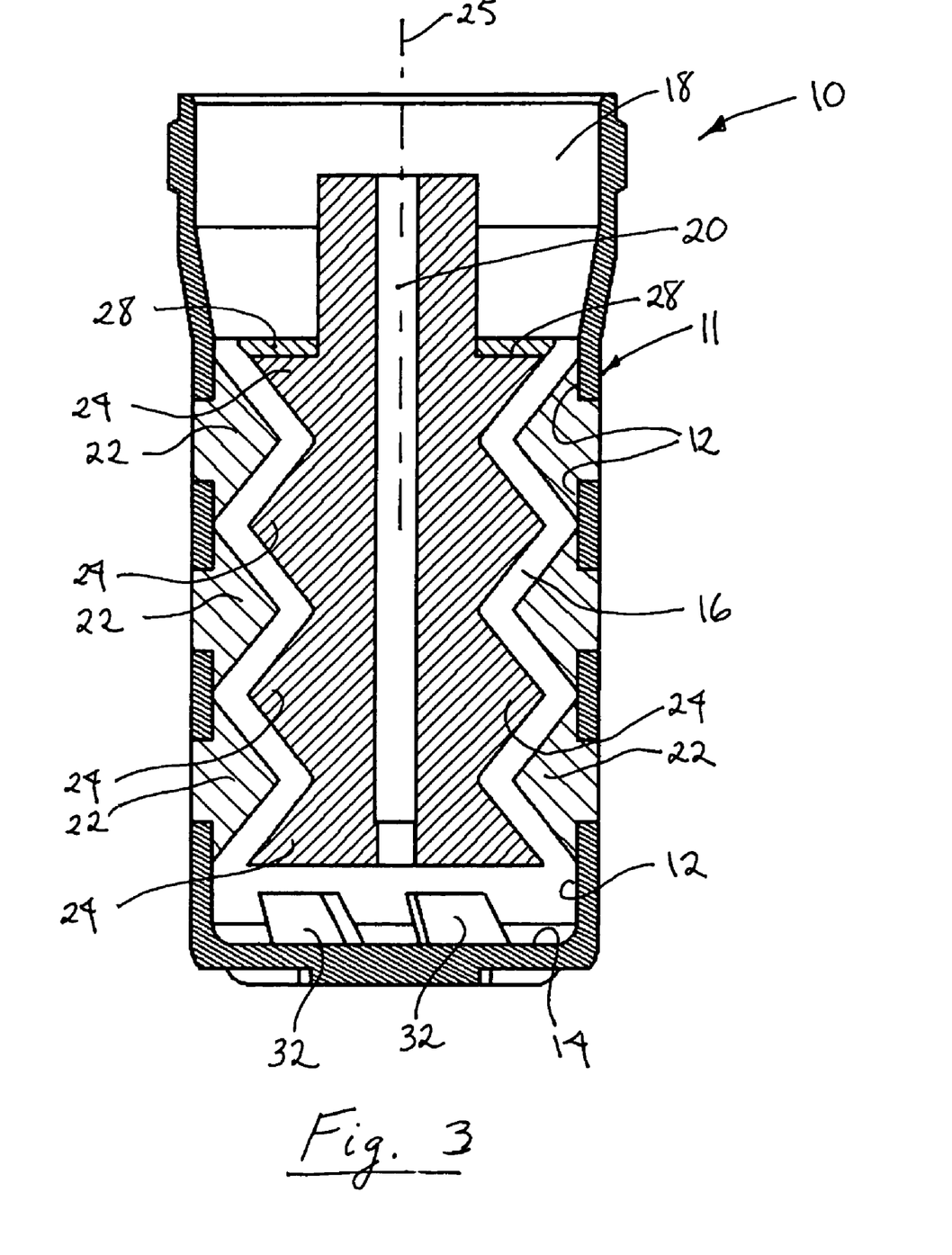
FIG. 3 is a schematic, cross-sectional illustration of the modified test cell shown in FIG. 2.

A particular implementation of the modified test cell 3 for high-pressure use is represented in FIGS. 2 and 3. A receptacle 10 preferably is a slurry cup 11 that is adapted to be used with a conventional viscometer of the high-pressure, high-temperature type referred to above. The receptacle 10 has a cylindrical side wall 12 extending from an end closed by a bottom wall 14 to an open end opposite the bottom wall 14. The side wall 12 and the bottom wall 14 have inner surfaces defining a cavity 16 in the receptacle 10. The cavity 16 receives the fluid to be tested. This cavity 16 provides a single continuous volume or cell for the fluid to be tested.

The modified test cell 3 of the FIG. 2 embodiment also includes means for closing the open end of the cavity 16 or receptacle 10 after the fluid is placed in the cavity 16. This closing means completes the definition of the outer boundaries of the continuous test chamber which can be pressurized above atmospheric pressure. In the implementation of FIG. 2, the closing means includes a conventional pressure sealed end closure 18 for the slurry cup 11 defining the receptacle 10. The closing means also includes the aforementioned support, which in the FIG. 2 implementation is an axial shaft, or axial support 20. This axial shaft hangs below the end closure 18 into the slurry cup 11 when the end closure 18 is connected to the slurry cup 11 in conventional manner to close the slurry cup 11. One example of the end closure 18 and the axial shaft 20 is found in the aforementioned Fann model 50 viscometer; however, other high-pressure, high-temperature devices can be used (and as mentioned, the present invention has application with devices that need not have high-pressure or high-temperature capability, such as an open-cup viscometer). It is to be understood that the receptacle 10 preferably includes, but is not required to include, a means for closing the open end thereof.

The modified test cell 3 shown in FIG. 2 further includes means for stirring fluid in the test chamber such that particulate in the fluid is suspended in the fluid during one period of time of the stirring but is not suspended in the fluid during another period of time of the stirring. This is implemented by at least one projection extending into the cavity 16 from the inner surface of the receptacle 10. In the preferred embodiment shown in FIG. 2, a plurality of substantially triangular metallic projections 22 are connected to the inner surface of the receptacle 10. Connection can be by any suitable means, including but not limited to welding to or integrally machining with the side wall 12. In other embodiments, a single projection 22 or different numbers of projections 22 can be used.

The FIG. 2 implementation also includes a projection extending laterally outward from the axial support 20. Projection 24 can be of the same or similar type and shape projection 22 and is connected to the axial shaft 20 in the FIG. 2 embodiment. While there may be two or more projections 24, preferably there is an even number of these projections. Connection can be by any suitable means, including but not limited to welding to or integrally machining with the axial support 20 or a mandrel that connects to the axial support 20.

The projections 22, 24 are large enough to generate a torque during stirring, but small enough to produce a torque reading within a desired range (the larger the projections, the larger the torque reading) and to leave a gap between the set of projections 22 and the set of projections 24 sufficient for the particulate material to pass through without bridging (e.g., three to four particle diameters). As shown in FIG. 2, projections 22 and 24 can be flat with planar surfaces.

The projections 24 operatively cooperate with the projections 22 to effect stirring of fluid in the slurry cup 11 in response to rotation of at least one of the slurry cup 11 or axial support 20. The slurry cup 11 is rotated so that the projections 22 principally effect the stirring, and the projections 24 are deflected in response to thereby sense torque. This rotation is achieved in conventional manner within the remainder of the viscometer used to implement the described embodiment of the present invention. The rotation is also obtained in a manner that permits an appropriate readout signal to be generated. Such rotation is typically within the range between one revolution per minute and one thousand revolutions per minute.

The FIG. 2 implementation also includes a flat disk or annular ring 28 mounted on the axial support 20. The ring 28 is positioned above the projections 24. Annular ring 28 performs the function of minimizing air or nitrogen entrainment and minimizing rod climbing. Without this ring, gas could be entrained into the fluid, and foam created during measuring can result in errors in torque reading. Also the foam will expand when the pressure is relieved at the end of the test. It will go into the closure means 18 of the instrument creating extensive cleanup and maintenance problems. Elastic fluids exhibit the rod climbing effect (also known as the Weissenberg effect) and crosslinked fluids are usually elastic. If the fluid is allowed to climb out of the measurement area, then errors in torque measurement occur.

In addition, the apparatus includes at least one projection for directing fluid flow that has at least one major surface angled or curved upward.

According to one embodiment of a projection for directing fluid flow, for example as shown in FIG. 2, one or more projections 30 can be provided that extend inward from the side wall 12. These projections 30 are mounted inclined at an angle with respect the center axis 25 of the cylindrical side wall 12 and shaft or axial support 20. In this manner the fluid contacting surfaces on these projections imparts stirring at least partially in an axial direction. This has been found to help lift particulate during stirring and help prevent substantial settling during the test.

Figure 4:
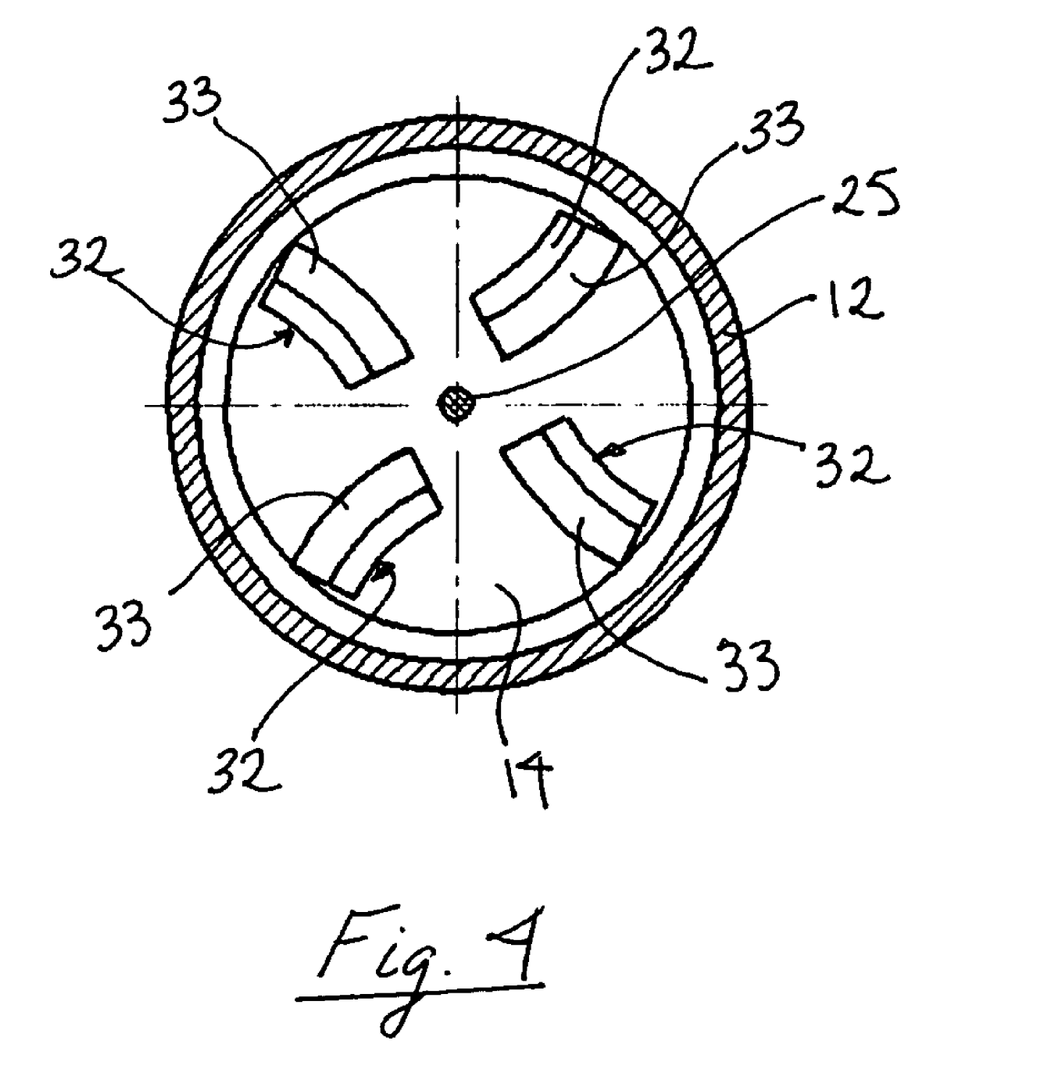
FIG. 4 is a schematic, top-view illustration of the bottom of the modified test cell shown in FIG. 2.

According to another embodiment of a projection for directing fluid flow, for example as shown in FIGS. 2-4, one or more projections 32 are mounded to extend generally upward from the bottom wall 14. Preferably, the projections 32 have curved or sloped surfaces 33 for directing fluid flow upward, so as to define an impeller on the bottom wall 14. Most preferably, the vanes or projections 32 are curved in an impeller shape and have a fluid contacting surface 33 that causes the fluid and particulate to flow axially upward away from the bottom wall 14. In this manner settling is inhibited when the cup 11 is rotated at a sufficient speed. While the vanes or projections 32 are illustrated as impeller shaped, it is anticipated that flat planar surfaced tabs, for example, could be used instead.

It is to be understood, of course, that while the presently preferred embodiment of the invention illustrated in FIGS. 2-4 includes both projections 30 and projections 32, it is believed that if desired and appropriately designed only one of these types of projections 30 or projections 32 would be required for directing fluid flow. It is also anticipated that the function of a stirring projection can be combined with the function of a projection for directing flow upward into a unitary structure.

As mentioned above, the embodiment of the present invention shown in FIGS. 1 and 2 includes a readout 8. This is part of a means for generating a signal in response to the stirring of the fluid during both the period during which particulate suspension occurs and the period during which particulate settling occurs. This is implemented in FIGS. 2-4 by using the one or more projections 24 on the axial shaft 20. For example, when the slurry cup 11 is rotated, torque is sensed through the axial shaft 20 in known manner. In an embodiment in which the axial shaft 20 is rotated to effect mixing by the one or more projections 24, torque is sensed through the slurry cup 11 or the axial shaft 20 in known manner. For the modified test cell 3 of the illustrated embodiment, the sensitivity of the readout 8 to such torque can be adjusted by using different strengths of springs or different sizes of flags (projections) or different transducers. An electric signal is generated in known manner in response to the deflection of the axial shaft 20; and the electric signal is used in known manner to create a display, such as an electronic display or a printed graph. As explained further hereinbelow, the display is maintained so that a graph of the response over time is obtained in accordance with the present invention.

The projections 22, 24, annular ring 28, projections 30, 32 and their inter-relationships with each other and the overall viscometer and method of the present invention can take different configurations, as will be appreciated by those of skill in the art.

Although illustrated with all of the above elements in combination, it is envisioned that measuring devices could be constructed with combinations having less than all the above elements, or a plurality of one or more of such elements.

The projections 22, 24 of the preferred embodiments are flat, planar members that are disposed with at least some projections disposed off set vertically (i.e., the major planar surfaces of such member are offset vertically with respect to the vertical axis 25). The projections 30, if present, also are preferably sized and positioned such that they would not interfere when rotated with the projections 22, 24.

The projections 22, 24, 30, and 32 are made of any material suitable for the substances, pressures, temperatures, and rotational characteristics to be encountered in using the present invention, as known in the art.

The preferred embodiments described above with reference to FIGS. 1 and FIGS. 2-4, and variations thereof as described herein, can be used to practice the methods described in U.S. Pat. No. 6,782,735 entitled Testing Device and Method for Viscosified Fluid Containing Particulate Material, which description is incorporated here by reference. In addition, however, the present device permits testing where suspension and resuspension steps are performed.

According to a method of the present invention, a fluid (either viscosified or not) containing particulate is placed in a container of the type described above. Preferably the method includes using in the viscometer an axial support or axial shaft as described herein.

The container, also called a slurry cup, holds the fluid, and the axial support extends into the fluid. The method further comprises creating relative movement between the container and the axial support. Relative movement is preferably created by rotating in known manner either the slurry cup of the viscometer or the axial support of the viscometer.

The method still further includes generating a measurement signal in response to a characteristic of the viscometer occurring by creating the relative movement. In the preferred embodiment, the measurement signal is an electric signal generated in response to torque related to creating relative movement between the container and the axial support and the projections thereof. Such electric signal can be generated with conventional torque sensing components of the viscometer which respond to deflection of the axial shaft by the force of the fluid against the projections on the axial shaft. Alternatively, the angular deflection may be read directly on a dial without the use of an electrical signal or signal generating means. Another preferred aspect of the foregoing is that the relative movement is created for a time during which the viscosity and/or elasticity of the fluid changes, which time includes a first period during which substantially all the particulate remains suspended in the fluid and which time includes a second period during which substantially all the particulate are allowed to settle out of suspension in the fluid (such as due to the viscosity and/or elasticity of the fluid being below the a level which will support the particulate). That is, rotation (e.g., by a motor connected and operated in known manner) continues throughout the range of viscosity change from the aforementioned first period through the aforementioned second period. Thus, the measurement signal taken over time has a characteristic which indicates the first period (an elastic particulate transport time period) and the second time period (a viscous settling time period).

The methods could also include additional measurement prior to the aforementioned first period (before crosslinking occurs), in that, the fluid could be placed in the cup and then particulates suspended and the fluid measured according to the particular feature of the present invention.

As apparent from the description of the invention above, stirring preferably includes either (1) rotating the slurry cup relative to a support disposed in the fluid, wherein the slurry cup has at least one projection extending inward into the fluid from the slurry cup and the support has at least two projections extending outward into the fluid from the support, or (2) rotating the support disposed in the fluid relative to the slurry cup. The former is typically preferred because of the lighter mass of the axial shaft structure relative to the slurry cup structure.

According to the method of the present invention a fluid (either viscosified or not) containing particulate is placed in a container of the type described herein. Preferably the method includes using in the viscometer an axial support or axial shaft as described herein. The container, also called a slurry cup, holds the fluid and particulates, in which case the fluid in its uncrosslinked state does not have sufficient viscosity to keep the particulates in suspension, and the axial support extends into the fluid. The method further comprises creating relative movement between the container and the axial support, and the projections thereof. At least one the projections and or vanes impart a stirring force in the fluid, sufficient to resuspend the particulates. Relative movement is preferably created by rotating in known manner either the slurry cup of the viscometer or the axial support of the viscometer. The method still further includes generating a measurement signal in response to a characteristic of the viscometer occurring by creating the relative movement. In the preferred embodiment, the measurement signal is an electric signal generated in response to torque related to creating relative movement between the container and the axial support and the projections thereof. Such electric signal can be generated with conventional torque sensing components of the viscometer which respond to deflection of the axial shaft by the force of the fluid against the projections on the axial shaft. Alternatively, the angular deflection may be read directly on a dial without the use of an electrical signal or signal generating means. Another preferred aspect of the foregoing is that the relative movement is created for a time during which the viscosity and/or elasticity of the fluid changes, which time includes a first period during which substantially all the particulate remains suspended in the fluid and which time includes a second period during which substantially all the particulate are allowed to settle out of suspension in the fluid (such as due to the viscosity and/or elasticity of the fluid being below the a level which will support the particulate). That is, rotation (e.g., by a motor connected and operated in known manner) continues throughout the range of viscosity change from the aforementioned first period through the aforementioned second period. Thus, the measurement signal taken over time has a characteristic which indicates the first period (an elastic particulate transport time period) and the second time period (a viscous settling time period). The methods could also include additional measurement prior to the aforementioned first period (before cross-linking occurs), in that, the fluid could be placed in the cup and then particulates suspended and the fluid measured according to the particular feature of the present invention.

Although the present invention is directed to the interoperative projections on the test chamber cup and axial shaft and the aforementioned method by which particle transport capability is determined, and by which crosslink time can be monitored (such as for real time use at an oil or gas well), other information can be obtained. For example, viscous and elastic properties can be determined by using the torque signal with known mathematical concepts (see, for example, U.S. Pat. No. 5,799,734; J. F. Steffe, Rheological Methods in Food Process Engineering (second edition), Freeman Press, East Lansing, Mich.; and K. L. Mackey, R. G. Morgan and J. F. Steffe, "Effects of Shear-Thinning Behavior on Mixer Viscometry Techniques," Michigan Agricultural Experiment Station Journal Article No. 12280, Apr. 1, 1987; the foregoing incorporated herein by reference).

Thus, the present invention is well adapted to carry out the objects and attain the ends and advantages mentioned above as well as those inherent therein. While preferred embodiments of the invention have been described for the purpose of this disclosure, changes in the construction and arrangement of parts and the performance of steps can be made by those skilled in the art, which changes are encompassed within the spirit of this invention as defined by the appended claims.

What is claimed is:

1. An apparatus for testing a rheological property of a fluid with a particulate, the apparatus comprising:
   (a) a receptacle having a cylindrical side wall enclosed by a bottom wall defining a cavity for receiving a fluid to be tested;
   (b) an axial support adapted to be positioned in the cavity of the receptacle, whereby relative rotational motion can be imparted to the receptacle and the axial support;
   (c) means for stirring fluid and particulate in the cavity when relative rotational motion is imparted to the receptacle and the axial support; and
   (d) means for directing rotational flow of fluid and particulate in the cavity toward an axial direction when the fluid and particulate is being stirred;
   further comprising means for minimizing gas entrainment and minimizing rod climbing, wherein the means for minimizing gas entrainment and minimizing rod climbing comprises: an annular ring on the axial support above the means for stirring.

2. An apparatus for testing a rheological property of a fluid with a particulate, the apparatus comprising:
   (a) a receptacle having a cylindrical side wall enclosed by a bottom wall defining a cavity for receiving a fluid to be tested;
   (b) an axial support adapted to be positioned in the cavity of the receptacle, whereby relative rotational motion can be imparted to the receptacle and the axial support;
   (c) means for stirring fluid and particulate in the cavity when relative rotational motion is imparted to the receptacle and the axial support; and
   (d) means for directing rotational flow of fluid and particulate in the cavity toward an axial direction when the fluid and particulate is being stirred;
   wherein the means for directing flow comprises: at least one projection for directing fluid flow that has at least one major surface angled or curved upward, wherein the means for directing flow further comprises: at least one projection on the bottom wall of the receptacle.

3. An apparatus for testing a rheological property of a fluid with a particulate, the apparatus comprising:
   (a) a receptacle having a cylindrical side wall enclosed by a bottom wall defining a cavity for receiving a fluid to be tested;
   (b) an axial support adapted to be positioned in the cavity of the receptacle, whereby relative rotational motion can be imparted to the receptacle and the axial support;
   (c) means for stirring fluid and particulate in the cavity when relative rotational motion is imparted to the receptacle and the axial support; and
   (d) means for directing rotational flow of fluid and particulate in the cavity toward an axial direction when the fluid and particulate is being stirred;
   wherein the means for directing flow comprises: at least one projection for directing fluid flow that has at least one major surface angled or curved upward, wherein the means for directing flow comprises: a plurality of projections on the bottom wall of the receptacle.

4. The apparatus according to claim 3, wherein the plurality of projections on the bottom wall of the receptacle define an impeller.

5. An apparatus for testing a rheological property of a fluid with a particulate, the apparatus comprising:
   (a) a receptacle having a cylindrical side wall enclosed by a bottom wall defining a cavity for receiving a fluid to be tested;
   (b) an axial support adapted to be positioned in the cavity of the receptacle, whereby relative rotational motion can be imparted to the receptacle and the axial support;
   (c) at least one inward projection extending inward from an inside surface of the receptacle;
   (d) at least one outward projection extending outward from the axial support; and
   (e) at least one projection for directing fluid flow that has at least one major surface angled or curved upward; and
   further comprising: an annular ring positioned on the axial support above the outward projection extending outward from the axial support.

* * * * *